(12) United States Patent
Inokuchi

(10) Patent No.: US 9,028,966 B2
(45) Date of Patent: May 12, 2015

(54) SILICONE FINE PARTICLES AND PRODUCTION METHOD THEREOF

(71) Applicant: Shin-Etsu Chemical Co., Ltd., Tokyo (JP)

(72) Inventor: Yoshinori Inokuchi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 78 days.

(21) Appl. No.: 13/644,562

(22) Filed: Oct. 4, 2012

(65) Prior Publication Data

US 2013/0095324 A1 Apr. 18, 2013

(30) Foreign Application Priority Data

Oct. 14, 2011 (JP) ................................. 2011-226664

(51) Int. Cl.
| | |
|---|---|
| C08G 77/14 | (2006.01) |
| C08L 83/04 | (2006.01) |
| C08J 3/12 | (2006.01) |
| A61Q 19/00 | (2006.01) |
| A61K 8/891 | (2006.01) |
| A61K 8/895 | (2006.01) |
| A61K 8/02 | (2006.01) |

(52) U.S. Cl.
CPC ............ *C08L 83/04* (2013.01); *Y10T 428/2995* (2013.01); *C08J 3/126* (2013.01); *C08J 2383/04* (2013.01); *C08J 2483/04* (2013.01); *A61Q 19/00* (2013.01); *A61K 8/891* (2013.01); *A61K 8/895* (2013.01); *A61K 8/025* (2013.01); *A61K 2800/10* (2013.01); *A61K 2800/624* (2013.01); *A61K 2800/654* (2013.01)

(58) Field of Classification Search
USPC ........... 428/402, 403, 407, 405; 427/212, 215
IPC ................. B05D 7/24; C08G 77/14; B32B 9/04
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 4,970,252 A * | 11/1990 | Sakuta et al. | ................ 524/268 |
| 5,538,793 A | 7/1996 | Inokuchi et al. | |
| 2004/0234477 A1 * | 11/2004 | Sakuta | ...................... 424/70.12 |
| 2006/0084758 A1 | 4/2006 | Morita | |

FOREIGN PATENT DOCUMENTS

| | | |
|---|---|---|
| EP | 2 357 024 A2 | 8/2011 |
| EP | 2357024 * | 8/2011 |
| JP | 7-196815 A | 8/1995 |
| JP | 3452562 B1 | 9/2003 |
| JP | 2004-210944 A | 7/2004 |
| JP | 2004-359592 A | 12/2004 |

OTHER PUBLICATIONS

European Search Report for corresponding European Patent Application No. 12187655.1, dated Jan. 30, 2013.

* cited by examiner

*Primary Examiner* — Leszek Kiliman
(74) *Attorney, Agent, or Firm* — Birch, Stewart, Kolasch & Birch, LLP

(57) ABSTRACT

A method for producing silicone fine particles is provided. The particle comprises a spherical fine silicone elastomer particle and polyorganosilsesquioxane particles attached to the surface of the spherical fine silicone elastomer particle. The polyorganosilsesquioxane particle has a particle size of 200 to 2,000 nm which is smaller than the spherical fine silicone elastomer particle. The method comprises the steps of adding an organotrialkoxysilane to water for hydrolysis, and adding spherical fine silicone elastomer particles having a volume average particle size of 0.5 to 100 μm, an anionic surfactant, and an alkaline substance to the organotrialkoxysilane hydrolysate and allowing the mixture to stand to thereby promote condensation of the organotrialkoxysilane hydrolysate so that the polyorganosilsesquioxane is deposited on the surface of the spherical fine silicone elastomer particles.

12 Claims, 2 Drawing Sheets

20 μm

US 9,028,966 B2

SILICONE FINE PARTICLES AND PRODUCTION METHOD THEREOF

CROSS-REFERENCE TO RELATED APPLICATION

This non-provisional application claims priority under 35 U.S.C. §119(a) on Patent Application No. 2011-226664 filed in Japan on Oct. 14, 2011, the entire contents of which are hereby incorporated by reference.

TECHNICAL FIELD

This invention relates to silicone fine particles comprising spherical fine silicone elastomer particles having polyorganosilsesquioxane particles having a particle size of 200 to 2,000 nm deposited on the silicone elastomer particles. This invention also relates to their production method.

BACKGROUND ART

Known silicone fine particles include fine particles having rubber elasticity (silicone elastomer fine particles) and fine particles of a polyorganosilsesquioxane resin, and these particles have been incorporated in cosmetic products for the purpose of giving dryness, smoothness, and other textures as well as spreadability with the product. More specifically, the inventors of the present invention proposed polyorganosilsesquioxane-coated silicone fine particles in JP-A H07-196815, and these particles are used in many cosmetic products due to the soft texture, reduced agglomeration, and excellent dispersion.

In the method proposed in JP-A H07-196815, an alkaline substance or an alkaline aqueous solution and an organotrialkoxysilane are added to an aqueous dispersion of spherical fine silicone elastomer particles to thereby promote hydrolytic condensation. The fine particles prepared by this method are spherical fine silicone elastomer particles coated with a polyorganosilsesquioxane, and the silicone elastomer particles have polyorganosilsesquioxane particles attached to their surface, and the polyorganosilsesquioxane particles have an approximate size of 100 nm. Due to the light scattering effects of the polyorganosilsesquioxane, natural finish with no unnatural gloss is realized when added in foundations and other makeup cosmetic products. In these days, such non-artificial natural finish (bare skin texture) is highly valued, and there is a demand for a higher light scattering property.

JP 3452562 proposes a method for producing spherical polyorganosilsesquioxane fine particles in the shape of pointed sugar candy balls having projections on the surface of the particles. JP-A 2004-359592 proposes a cosmetic product having such spherical polyorganosilsesquioxane fine particles incorporated therein, and the projections on the surface are said to dramatically improve the optical properties and camouflage pores and wrinkles of the skin. Particles having the projections with the diameter of 400 nm, 600 nm, and 800 nm are described, and provision of the projections with such diameter not shorter than the wavelength (approximately 400 to 800 nm in the case of visible light) are estimated to contribute for the high light scattering property. The polyorganosilsesquioxane fine particle, however comprises a resinous hard material, and it can not be provided with a soft texture.

SUMMARY OF INVENTION

Technical Problem

The present invention has been completed in view of the situation as described above, and an object of the present invention is to provide silicone fine particles which are expected to exhibit high light scattering as well as soft texture in cosmetic products. Another object of the present invention is to provide a method for producing such silicone fine particles.

Solution to Problem

In order to attain the objects as described above, the inventors of the present invention conducted an intensive study, and found that the objects as described above can be realized by the silicone fine particles and their production method as described below. The present invention has been completed in view of such findings.

First, the present invention provides silicone fine particles comprising 100 parts by weight of spherical fine silicone elastomer particles having a volume average particle size of 0.5 to 100 μm and 1 to 100 parts by weight of a polyorganosilsesquioxane deposited on the surface of the silicone particles. The polyorganosilsesquioxane is in the form of particles. The particle size of 200 to 2,000 nm which is smaller than the spherical fine silicone elastomer particles.

Second, the present invention provides a method for producing silicone fine particles. Each particle comprises a spherical fine silicone elastomer particle and polyorganosilsesquioxane particles attached to the surface of the spherical fine silicone elastomer particles. The polyorganosilsesquioxane particle has a particle size in the range of 200 to 2,000 nm which is smaller than the spherical fine silicone elastomer particle. The method comprises the steps of adding an organotrialkoxysilane to water for hydrolysis, and adding spherical fine silicone elastomer particles having a volume average particle size of 0.5 to 100 μm, an anionic surfactant, and an alkaline substance to the organotrialkoxysilane hydrolysate and allowing the mixture to stand to thereby promote condensation of the organotrialkoxysilane hydrolysate so that the polyorganosilsesquioxane is deposited on the surface of the spherical fine silicone elastomer particle.

Advantageous Effects of Invention

The silicone fine particles of the present invention can be blended in cosmetic products such as makeup products to realize soft, dry, and smooth textures as well as improved spreading. The silicone fine particles of the present invention are also expected to exhibit high light scattering performance owing to the increased particle size of the polyorganosilsesquioxane particles attached to the surface of the spherical fine silicone elastomer particles, and accordingly, the product is expected to hide morphological troubles of the skin such as wrinkles, pores, roughness as well as color troubles of the skin such as blotches and freckles to provide natural finish.

DESCRIPTION OF EMBODIMENTS

Figure 1:
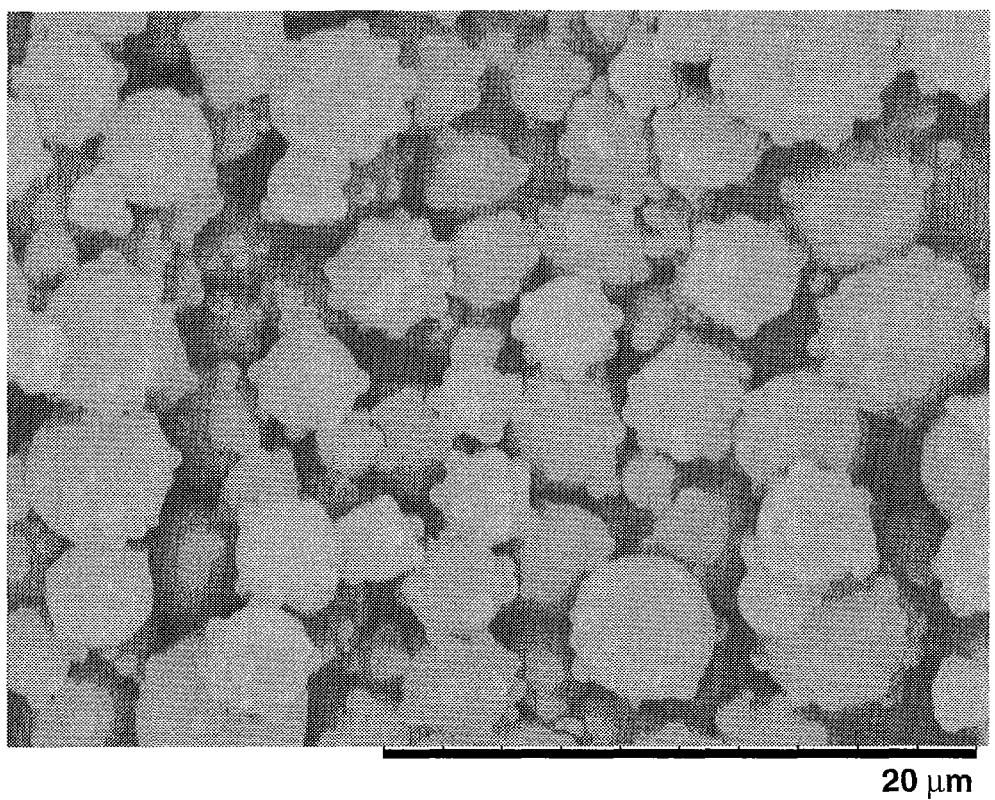
FIG. 1 is a photomicrograph of the silicone fine particles of Example 1.

Next, the present invention is described in detail.
Silicone Fine Particles
The silicone fine particles of the present invention comprises spherical fine silicone elastomer particles and polyorganosilsesquioxane particles having a size of 200 to 2,000 nm which is smaller than the spherical fine silicone elastomer particles. The polyorganosilsesquioxane particles are attached to the surface of the spherical fine silicone elastomer particles, and the amount of the polyorganosilsesquioxane is such that 1 to 100 parts by weight, and preferably 5 to 70 parts by weight of the polyorganosilsesquioxane is present in relation to 100 parts by weight of the spherical fine silicone elastomer particles. When the polyorganosilsesquioxane is less than 1 part by weight, light scattering property and smoothness as well as dryness of the resulting fine particles will be insufficient while the use at an amount in excess of 100 parts by weight leads to loss of soft texture.

Spherical Fine Silicone Elastomer Particles

In the silicone fine particle of the present invention, the spherical fine silicone elastomer particles having the polyorganosilsesquioxane attached on the surface has a volume average particle size of 0.5 to 100 μm, and preferably 1 to 40 μm. When the volume average particle size is less than 0.5 μm, the resulting silicone fine particles tend to agglomerate, and the particles is not likely to be dispersed into primary particles, and also, the resulting particles have reduced dryness. When the volume average particle size is in excess of 100 μm, the resulting silicone fine particles will have poor dryness and smoothness, and occasionally, increased roughness. The method used for measuring the average particle size may vary by the particle size, and the particles having a diameter of at least 1 μm is measured by means of electric resistance, and the particles having a diameter of less than 1 μm is measured by laser diffraction/scattering. In the present invention, "spherical" and "sphere" mean not only real sphere but also include deformed sphere wherein major axis/minor axis (aspect ratio) on average is typically in the range of 1 to 4, preferably 1 to 2, more preferably 1 to 1.6, and even more preferably 1 to 1.4. The shape of the fine particles may be confirmed by observing the fine particle with an optical microscope or electron microscope.

The silicone elastomer constituting the spherical fine silicone elastomer particles preferably has no tackiness and the rubber hardness measured by Durometer A defined in JIS K 6253 is preferably in the range of 5 to 90, and more preferably 10 to 80. When the rubber hardness is less than 5, the resulting silicone fine particles tend to become agglomerated, and dispersion into primary particles will be difficult with decrease in the dryness. The rubber hardness in excess of 90 will invite loss of soft texture.

The silicone elastomer is a cured product containing a linear organosiloxane block represented by the formula: —(R$^1$$_2$SiO$_{2/2}$)$_n$— wherein R$^1$ is a substituted or unsubstituted monovalent hydrocarbon group containing 1 to 30 carbon atoms, and n is a positive number of 5 to 5,000.

Examples of the R$^1$ include alkyl groups such as methyl group, ethyl group, propyl group, butyl group, pentyl group, hexyl group, heptyl group, octyl group, decyl group, undecyl group, didecyl group, tetradecyl group, pentadecyl group, hexadecyl group, heptadecyl group, octadecyl group, nonadecyl group, eicosyl group, heneicosyl group, docosyl group, tricosyl group, tetracosyl group, and triacontyl group; aryl groups such as phenyl group, tolyl group, and naphthyl group; aralkyl groups such as benzyl group and phenethyl group; alkenyl groups such as vinyl group and ally group; cycloalkyl groups such as cyclopentyl group, cyclohexyl group, and cycloheptyl group; and any one of such groups having all or a part of the hydrogen atoms bonded to the carbon atoms substituted with an atom such as a halogen atom (for example, fluorine atom, chlorine atom, bromine atom, and iodine atom) and/or a substituent such as acryloyloxy group, methacryloyloxy group, epoxy group, glycidoxy group, or carboxyl group.

The silicone elastomer is the one obtained from a curable liquid silicone composition, and the curing is accomplished, for example, by condensation reaction between methoxysilyl group (≡SiOCH$_3$) and hydroxysilyl group (SiOH) or the like, radical reaction between mercaptopropylsilyl group (≡Si—C$_3$H$_6$SH) and vinylsilyl group (≡SiCH═CH$_2$), addition reaction between vinylsilyl group (≡SiCH═CH$_2$) and hydrosilyl group (≡SiH). In view of reactivity, the silicone elastomer is preferably the one which cures by addition reaction.

When the silicone elastomer is produced by the addition reaction curing, a liquid silicone composition comprising the combination of an organopolysiloxane represented by the average formula: R$^2$$_a$R$^3$$_b$SiO$_{(4-a-b)/2}$ having at least 2 monovalent olefinic unsaturated groups per molecule and an organohydrogenpolysiloxane represented by the average formula: R$^4$$_c$H$_d$SiO$_{(4-c-d)/2}$ having at least 3 hydrogen atoms bonded to silicon atoms per molecule; or the combination of an organopolysiloxane represented by the average formula: R$^2$$_a$R$^3$$_b$SiO$_{(4-a-b)/2}$ having at least 3 monovalent olefinic unsaturated groups per molecule and an organohydrogenpolysiloxane represented by the average formula: R$^4$$_c$H$_d$SiO$_{(4-c-d)/2}$ having at least 2 hydrogen atoms bonded to silicon atoms per molecule may be cured by addition reaction in the presence of a platinum group metal catalyst. In this liquid silicone composition, the organopolysiloxane having the monovalent olefinic unsaturated group and the organohydrogenpolysiloxane are incorporated such that 0.5 to 2 hydrosilyl groups (i.e., SiH groups) are present in relation to 1 monovalent olefinic unsaturated group.

In the formula, R$^2$ is a substituted or unsubstituted monovalent hydrocarbon group containing 1 to 30 carbon atoms excluding the aliphatic unsaturated group, R$^3$ is a monovalent olefinic unsaturated group such as alkenyl group containing 2 to 6 carbon atoms. Letters a and b are independently a positive number of 0<a<3, 0<b<3, and 0.1≤a+b≤3, and preferably, 0<a≤2.295, 0.005≤b<2.3, and 0.5≤a+b≤2.3. R$^4$ is a monovalent hydrocarbon group containing 1 to 30 carbon atoms excluding the aliphatic unsaturated group. Letters c and d are independently a positive number of 0<c<3, 0<d<3, and 0.1≤c+d≤3, and preferably, 0<c≤2.295, 0.005≤d<2.3, and 0.5≤c+d≤2.3.

Examples of the R$^2$ include alkyl groups such as methyl group, ethyl group, propyl group, butyl group, pentyl group, hexyl group, heptyl group, octyl group, decyl group, undecyl group, didecyl group, tetradecyl group, pentadecyl group, hexadecyl group, heptadecyl group, octadecyl group, nonadecyl group, eicosyl group, heneicosyl group, docosyl group, tricosyl group, tetracosyl group, and triacontyl group; aryl groups such as phenyl group, tolyl group, and naphthyl group; aralkyl groups such as benzyl group and phenethyl group; cycloalkyl groups such as cyclopentyl group, cyclohexyl group, and cycloheptyl group; and any one of such groups having all or a part of the hydrogen atoms bonded to the carbon atoms substituted with an atom such as a halogen atom (for example, fluorine atom, chlorine atom, bromine atom, and iodine atom) and/or a substituent such as acryloyloxy group, methacryloyloxy group, epoxy group, glycidoxy group, or carboxyl group. In commercial point of view, at least 50% by mole of all R$^2$ group is preferably methyl group.

Examples of R$^3$ include vinyl group, allyl group, propenyl group, butenyl group, pentenyl group, and hexenyl group, and R$^3$ is preferably vinyl group for commercial scale production.

Examples of $R^4$ may be the same as those mentioned for $R^2$.

The organopolysiloxane having the olefinic unsaturated group and the organohydrogenpolysiloxane may preferably have a viscosity at 25° C. of up to 100,000 mm²/s since particles with narrow distribution can not be produced by the method as described below when the viscosity is in excess of 100,000 mm²/s. The organopolysiloxane having the olefinic unsaturated group and the organohydrogenpolysiloxane may have any of straight chain, cyclic, and branched structure, and the preferred is the straight chain structure. The viscosity is the value measured by Ostwald viscometer.

As described above, the organopolysiloxane having the olefinic unsaturated group needs to be the combination of an organopolysiloxane having at least 2 monovalent olefinic unsaturated groups per molecule and an organohydrogenpolysiloxane having at least 3 hydrogen atoms bonded to silicon atoms per molecule, or the combination of an organopolysiloxane having at least 3 monovalent olefinic unsaturated groups per molecule and an organohydrogenpolysiloxane having at least 2 hydrogen atoms bonded to silicon atoms per molecule. In the case of other combination and the structure of the polysiloxanes, the resulting cured elastomer will be tacky.

The platinum group metal catalyst may be a hydrosilylation catalyst known in the art, and examples include platinum group metals (simple substance) such as platinum (including platinum black), rhodium, and palladium; platinum chlorides such as $H_2PtCl_4 \cdot kH_2O$, $H_2PtCl_6 \cdot kH_2O$, $NaHPtCl_6 \cdot kH_2O$, $KHPtCl_6 \cdot kH_2O$, $Na_2PtCl_6 \cdot kH_2O$, $K_2PtCl_4 \cdot kH_2O$, $PtCl_4 \cdot kH_2O$, $PtCl_2$, $Na_2HPtCl_4 \cdot kH_2O$ (wherein k is an integer of 0 to 6, and preferably 0 or 6), chloroplatinic acid, and chloroplatinate salt; alcohol-modified chloroplatinic acid (see U.S. Pat. No. 3,220,972); complex of chloroplatinic acid and an olefin (see U.S. Pat. No. 3,159,601, U.S. Pat. No. 3,159,662, U.S. Pat. No. 3,775,452); a platinum group metal such as platinum black and palladium loaded on a carrier such as alumina, silica, and carbon; rhodium-olefin complex; chlorotris(triphenylphosphine) rhodium (Wilkinson catalyst); platinum chloride, chloroplatinic acid, and complex of chloroplatinate salt and a vinyl group-containing siloxane, and in particular, a vinyl group-containing cyclic siloxane.

The platinum group metal catalyst may be incorporated at an amount effective as a hydrosilylation catalyst, and typically at an amount such that amount in terms of platinum group metal in the catalyst is 0.1 to about 500 ppm, preferably 0.5 to about 200 ppm, and more preferably 1 to about 100 ppm in relation to the total amount of the liquid silicone composition.

The spherical fine silicone elastomer particles of the present invention may contain silicone oil, organosilane, inorganic powder, organic powder, and the like in the particles.

The spherical fine silicone elastomer particles of the present invention may be prepared in the form of an aqueous dispersion by a method known in the art. For example, when the silicone elastomer is prepared by addition reaction curing, a surfactant and water may be added to the liquid silicone composition comprising an organopolysiloxane having an olefinic unsaturated group and an organohydrogenpolysiloxane as described above for emulsification, and a platinum group metal catalyst may be added to the emulsion to facilitate the addition.

The surfactant used is a nonionic surfactant, an anionic surfactant, or an amphoteric surfactant. Use of a cationic surfactant may result in the suppression of the action of the anionic surfactant used in the step of coating the polyorganosilsesquioxane as described below, and also, in the loss of dispersibility of the spherical fine silicone elastomer particles upon mixing with the anionic surfactant, and hence, in the agglomaration.

Examples of the nonionic surfactant include polyoxyethylene alkyl ether, polyoxyethylene polyoxypropylene alkyl ether, polyoxyethylene alkyl phenyl ether, polyethylene glycol fatty acid ester, sorbitan fatty acid ester, polyoxyethylene sorbitan fatty acid ester, polyoxyethylene sorbit fatty acid ester, glycerin fatty acid ester, polyoxyethylene glycerin fatty acid ester, polyglycerin fatty acid ester, propylene glycol fatty acid ester, polyoxyethylenecastor oil, polyoxyethylene-hydrogenated castor oil, polyoxyethylene-hydrogenated castor oil fatty acid ester, polyoxyethylene alkylamine, polyoxyethylene fatty acid amide, polyoxyethylene-modified organopolysiloxane, and polyoxyethylene polyoxypropylene-modified organopolysiloxane. Examples of the anionic surfactant include alkyl sulphate, polyoxyethylene alkyl ether sulphate, polyoxyethylene alkylphenyl ether sulphate, N-acyltaurine, alkyl benzenesulphonate, polyoxyethylene alkylphenyl ether sulfonate salt, α-olefin sulfonate salt, alkyl naphthalene sulfonate salt, alkyldiphenyl ether disulfonate salt, dialkylsulfosuccinate salt, monoalkylsulfosuccinate salt, polyoxyethylene alkyl ether sulfosuccinate salt, fatty acid salt, polyoxyethylene alkyl ether acetate, N-acylamino acid salt, N-acylmethyl alanine salt, alkenyl succinate salt, alkyl phosphate, and polyoxyethylene alkyl ether phosphate. Examples of the amphoteric surfactant include alkyldimethylamine oxide, carboxy betaine, alkyl amide propyldimethylcarboxy betaine, alkylhydroxy sulfobetaine, and alkylcarboxymethyl hydroxyethyl imidazolinium betaine.

The surfactant as described above may be used alone or in combination of two or more, and preferred is the use of a nonionic surfactant which is capable of emulsifying the liquid silicone composition into fine particles by using a small amount. Excessive use of the surfactant results in the difficulty of attaching the polyorganosilsesquioxane on the surface of the spherical fine silicone elastomer particles by the production method as described below. Amount of the surfactant used is preferably up to 20 parts by weight in relation to 100 parts by weight of the liquid silicone composition. Since emulsification into fine particles is difficult by the use at less than 0.01 part by weight, the amount used is preferably in the range of 0.01 to 20 parts by weight, and more preferably 0.05 to 5 parts by weight.

The emulsification may be accomplished by using a emulsifying disperser commonly used in the art such as a high speed rotary centrifugal injection agitator such as homodisper, high speed rotary shear agitator such as homomixer, high pressure jet emulsifying disperser such as homogenizer, colloid mill, and ultrasound emulsifier.

When the platinum group metal catalyst has poor dispersibility in water, the platinum group metal catalyst may be added to the emulsion as a solution in the surfactant. Exemplary surfactants include those as mentioned above, and the most preferred are nonionic surfactants.

The addition reaction may be conducted at room temperature. However, when the reaction is not completed, the reaction may conducted by heating to a temperature of less than 100° C.

Polyorganosilsesquioxane

In the silicone fine particle of the present invention, the polyorganosilsesquioxane attached on the surface of the spherical fine silicone elastomer particles is in particulate shape with the diameter of 200 to 2,000 nm, and preferably 300 to 1,000 nm, and the polyorganosilsesquioxane should be smaller than the spherical fine silicone elastomer particle. When the polyorganosilsesquioxane is smaller than 200 nm or larger than 2,000 nm, light scattering property will be poor, while soft texture will be lost when the polyorganosilsesquioxane is larger than the spherical fine silicone elastomer particle. The polyorganosilsesquioxane may be sparsely or densely attached to the surface of the spherical fine silicone elastomer particles. Although the shape of the polyorganosilsesquioxane is not particularly limited, the polyorganosilsesquioxane is preferably spherical or semi-spherical. The diameter, shape, and amount of the polyorganosilsesquioxane can be confirmed by observing the fine particles using an electron microscope.

A polyorganosilsesquioxane is a resinous solid comprising units represented by the formula: $R^5SiO_{3/2}$, which are crosslinked to form a three dimensional network. In the present invention, $R^5$ in the formula is a substituted or unsubstituted monovalent hydrocarbon group containing 1 to 20 carbon atoms. Examples of the $R^5$ include alkyl groups such as methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group, and eicosyl group; alkenyl groups such as vinyl group and allyl group; aryl groups such as phenyl group, tolyl group, and naphthyl group; aralkyl groups such as benzyl group and phenethyl group; cycloalkyl groups such as cyclopentyl group, cyclohexyl group, and cycloheptyl group; and any one of such hydrocarbon groups having all or a part of the hydrogen atoms bonded to the carbon atom of the group substituted with an atom such as a halogen atom (for example, fluorine atom, chlorine atom, bromine atom, or iodine atom) and/or a substituent such as amino group, acryloyloxy group, methacryloyloxy group, epoxy group, glycidoxy group, mercapto group, or carboxyl group. In view of coating the polyorganosilsesquioxane by the method as described below, at least 50% by mole, more preferably at least 80% by mole, and still more preferably at least 90% by mole of the $R^5$ is methyl group, vinyl group, or phenyl group.

The polyorganosilsesquioxane may contain at least one member selected from $R^5{}_2SiO_{2/2}$ unit, $R^5{}_3SiO_{1/2}$ unit, and $SiO_{4/2}$ unit in addition to the $R^5SiO_{3/2}$ unit to the extent not adversely affecting the properties such as non-agglomeration and dispersibility of the resulting silicone fine particle, texture such as dryness and smoothness, and soft texture. In such polyorganosilsesquioxane, the content of the $R^5SiO_{3/2}$ unit is preferably 70 to 100% by mole, and more preferably 80 to 100% by mole in the entire siloxane units.

Production Method

The silicone fine particles of the present invention may be prepared by adding an organotrialkoxysilane to water for hydrolysis, and adding spherical fine silicone elastomer particles having a volume average particle size of 0.5 to 100 μm, an anionic surfactant, and an alkaline substance, and allowing the dispersion to stand for condensation of the hydrolyzed organotrialkoxysilane to thereby attach the polyorganosilsesquioxanes to the surface of the spherical fine silicone elastomer particle.

Even with the use of an anionic surfactant, the production of silicone fine particles of the present invention where polyorganosilsesquioxane particles having a size of 200 to 2,000 nm are attached to the surface of the spherical fine silicone elastomer particles is difficult by the procedure as disclosed in JP-A H07-196815 where an organotrialkoxysilane is added to water, spherical fine silicone elastomer particle, and an alkaline substance with stirring to thereby promote hydrolytic condensation.

Organotrialkoxysilane

Examples of the organotrialkoxysilane include those represented by the formula: $R^5Si(OR^6)_3$ wherein $R^5$ is as defined above, and $R^6$ is an unsubstituted monovalent hydrocarbon group containing 1 to 6 carbon atoms. Examples of $R^6$ include methyl group, ethyl group, propyl group, butyl group, pentyl group, and hexyl group, and preferred is methyl group in view of reactivity. When further incorporation of at least one member selected from $R^5{}_2SiO_{2/2}$ unit, $R^5{}_3SiO_{w/2}$ unit, and $SiO_{4/2}$ unit in the polyorganosilsesquioxane is desired, at least one member selected from the corresponding $R^5{}_2Si(OR^6)_2$, $R^5{}_3SiOR^6$, and $Si(OR^6)$, (wherein $R^5$ and $R^6$ are as defined above) may be added. When $R^5Si(OR^6)_3$ and at least one member of $R^5{}_2Si(OR^6)_2$, $R^5{}_3SiOR^6$, and $Si(OR^6)$, are used as the starting material for the polyorganosilsesquioxane, the content of the $R^5Si(OR^6)_3$ is preferably 70 to 100% by mole, and more preferably 80 to 100% by mole in the entire starting material.

The organotrialkoxysilane is preferably added at an amount such that the amount of the polyorganosilsesquioxane is in the range of 1 to 100 parts by weight, and preferably 5 to 70 parts by weight in relation to 100 parts by weight of the spherical fine silicone elastomer particles.

First, an organotrialkoxysilane is added to water, and hydrolysis of the organotrialkoxysilane is promoted with agitation by using an agitator having propeller, flat plate, or other puddles commonly used in the art. The water is added at least at the same amount as the alkoxy group in the organotrialkoxysilane. There is no particular upper limit for the water content, and the water may be added at an amount up to 10,000 folds by weight of the alkoxy group in the organoalkoxysilane. The organotrialkoxysilane may be added at once, or gradually in slow pace. On the contrary, the water may be added to the organotrialkoxysilane, or the organotrialkoxysilane and the water may be simultaneously added to the reaction vessel. The temperature used for this reaction is not particularly limited, and the reaction may be accomplished at a temperature in the range of 0 to 100° C. If desired, a small amount of acid may be added for the promotion of the reaction.

Spherical Fine Silicone Elastomer Particles

The spherical fine silicone elastomer particles used are those having a volume average particle size of 0.5 to 100 μm, and the use of those prepared in the form of an aqueous dispersion as described above is preferable.

The spherical fine silicone elastomer particles are mixed with the aqueous solution of the hydrolyzed organotrialkoxysilane (organotrialkoxysilane hydrolysate) obtained by the hydrolysis of the organotrialkoxysilane as described above. If the spherical fine silicone elastomer particles are incorporated before the hydrolysis, the organotrialkoxysilane is absorbed into the interior of the spherical fine silicone elastomer particles and the polyorganosilsesquioxane will not be attached to the surface of the spherical fine silicone elastomer particles.

The spherical fine silicone elastomer particles are preferably added at an amount of 1 to 40 parts by weight, and more preferably 3 to 20 parts by weight in relation to 100 parts by weight of the water at the timing of the addition of the alkaline substance. When added at an amount of less than 1 part by weight, desired silicone fine particles are not formed at a high efficiently, while addition in excess of 40 parts by weight leads to difficulty of attaching the polyorganosilsesquioxane resin on the surface of the spherical fine silicone elastomer particles. Water may be added when the spherical fine silicone elastomer particles are in excess in relation to the water.

Anionic Surfactant

The anionic surfactant has the function of facilitating attachment of the polyorganosilsesquioxane on the surface of the spherical fine silicone elastomer particles and increasing of the diameter of the polyorganosilsesquioxane. Single anionic surfactant or two or more types of anionic surfactants may be used in combination. The anionic surfactant may be used so that 0.001 to 1 part by weight, and more preferably 0.01 to 0.5 part by weight of the anionic surfactant is present in relation to 100 parts by weight of the water at the timing of the alkali addition as described below. When used at less than 0.001 part by weight, the increase in the diameter of the polyorganosilsesquioxane is not realized, while the addition in excess of 1 part by weight results in the failure of the attachment of the polyorganosilsesquioxane to the surface of the spherical fine silicone elastomer particles.

The anionic surfactant used is not particularly limited, and examples of the anionic surfactant are those as mentioned above. Preferably, the anionic surfactant is N-acyltaurine, N-acylamino acid salt, N-acylmethyl alanine salt, alkyl phosphate, or polyoxyethylene alkyl ether phosphate.

The anionic surfactant is added and dissolved in water before the addition of the alkaline substance as described below. In other words, the anionic surfactant may be dissolved in water before the mixing with the organotrialkoxysilane, or the anionic surfactant may be dissolved in the aqueous dispersion of the spherical fine silicone elastomer particles. Alternatively, the anionic surfactant may be added and dissolved in the aqueous solution of the hydrolyzed organotrialkoxysilane after adding the spherical fine silicone elastomer particles.

Alkaline Substance

The alkaline substance acts as a condensation catalyst of the hydrolyzed organotrialkoxysilane to produce the polyorganosilsesquioxane. Single alkaline substance or two or more types of alkaline substances may be used in combination. The alkaline substance may be directly added to the reaction system while the alkaline substance is preferably added in the form of an aqueous solution since quick and uniform dissolution in water is necessary as described below. The alkaline substance is preferably added at an amount such that pH of the water (including the water constituting the aqueous solution if the alkaline substance is added in the form of an aqueous solution) at the addition of the alkaline substance is in the range of 9.0 to 12.0, and more preferably 9.5 to 11.5. When the amount of the alkaline substance is less than the amount corresponding to the pH of 9.0, the progress of the condensation of the organotrialkoxysilane will be extremely slow, while the amount of the alkaline substance in excess of the amount corresponding to the pH of 12.0 may lead to difficulty in the attaching of the polyorganosilsesquioxane to the surface of the spherical fine silicone elastomer particles and difficulty in increasing the diameter of the polyorganosilsesquioxane.

The alkaline substance is not particularly limited, and examples include alkaline metal hydroxides such as potassium hydroxide, sodium hydroxide, and lithium hydroxide; alkaline earth metal hydroxides such as calcium hydroxide and barium hydroxide; alkaline metal carbonates such as potassium carbonate and sodium carbonate; ammonia; tetraalkylammonium hydroxides such as tetramethylammonium hydroxide and tetraethylammonium hydroxide; and amines such as monomethylamine, monoethylamine, monopropylamine, monobutylamine, monopentylamine, dimethylamine, diethylamine, trimethylamine, triethanolamine, and ethylenediamine. Among these, the most preferred is ammonia since in view of the easy removal from the resulting silicone fine particle powder by volatilization. The ammonia used may be commercially available ammonia solution.

The alkaline substance is added to the solution containing the water, the hydrolysate of the organotrialkoxysilane, the spherical fine silicone elastomer particles, and the anionic surfactant with agitation using an agitator having propeller, flat plate, or other puddles commonly used in the art. The condensation of the hydrolysate of the organotrialkoxysilane proceeds after the addition of the alkaline substance to form polyorganosilsesquioxane, and the agitation should be stopped before the formation of the polyorganosilsesquioxane. If the solution is flowing at a high speed during the formation of the polyorganosilsesquioxane, the polyorganosilsesquioxane will not be steadily attached to the surface of the spherical fine silicone elastomer particles. The agitation after the addition of the alkaline substance may be continued only for the time required for uniform dissolution of the alkaline substance in the water. However, very slow stirring may be continued as long as the deposition of the polyorganosilsesquioxane on the surface of the spherical fine silicone elastomer particles is not interrupted. Temperature in this stage is preferably in the range of 0 to 60° C., and preferably 0 to 40° C. Increase in the diameter of the polyorganosilsesquioxane particles attached on the surface of the spherical fine silicone elastomer particles will be difficult when the temperature is 60° C. or higher.

The solution is allowed to stand until the polyorganosilsesquioxane (having the polyorganosilsesquioxane attached to the surface of the spherical fine silicone elastomer particles) is formed. More specifically, the solution is allowed to stand preferably for 10 minutes to 24 hours. If desired, addition of the alkaline substance, heating to a temperature of 40 to 100° C., further agitation, or the like may be conducted for the completion of the condensation.

Pulverization

After the condensation, the water may be removed from the aqueous dispersion to produce the silicone fine particles of the present invention. The water removal may be accomplished, for example, by heating the resulting aqueous dispersion under normal or reduced pressure. More specifically, water may be removed from the aqueous dispersion, for example, by allowing the dispersion to stand at an elevated temperature, by agitating and moving the dispersion at an elevated temperature, by spraying and dispersing the dispersion into high temperature water, for example, by using a spray dryer, or by using a fluidized heating medium. The aqueous dispersion may be preliminary concentrated before the water removal process, for example, by thermal dehydration, separation by filtration or centrifugation, or decantation, and if necessary, the dispersion may be washed with water or alcohol.

When the product left after removing moisture from the resulting aqueous dispersion is agglomerated, the product may be pulverized by using a pulverizer such as jet mill, ball mill, or hammer mill.

EXAMPLES

Next, the present invention is described in further detail by referring to Examples and Comparative Examples which by no means limit the scope of the present invention. In the following Examples and Comparative Examples, viscosity is the dynamic viscosity value measure by Ostwald viscometer at 25° C., and "%" representing the concentration and content is "% by weight".

Example 1

500 g of methylvinylpolysiloxane represented by the following formula (1) having a viscosity of 600 mm²/s and 20 g of methylhydrogenpolysiloxane represented by the following formula (2) having a viscosity of 30 mm²/s (at an amount such that 1.11 hydrosilyl groups (SiH groups) were present in relation to 1 olefinic unsaturated group, i.e., 1 vinyl group) were charged in 1 liter glass beaker, and the mixture was agitated at 2,000 rpm by a homomixer for dissolution. Next, 3 g of polyoxyethylene lauryl ether (ethylene oxide addition, 9 mole) and 60 g of water were added, and the mixture was agitated at 6,000 rpm by a homomixer to prepare an oil-in-water emulsion with an increased viscosity. The agitation of the mixture was continued for further 15 minutes. When 415 g of water was added with agitation at 2,000 rpm, consistent white emulsion was obtained. This emulsion was moved to a 1 liter glass flask equipped with an agitator having an anchor-shaped agitator blade, and the temperature was adjusted to 15 to 20° C. A mixed solution of 1 g of toluene solution of chloroplatinic acid-olefin complex (platinum content, 0.5%) and 1 g of polyoxyethylene lauryl ether (ethylene oxide addition, 9 mole) was added with agitation, and the mixture was agitated at the same temperature for 12 hours to prepare an aqueous dispersion of the silicone elastomer fine particles.

The silicone elastomer fine particles in the resulting aqueous dispersion were observed for their shape with an optical microscope, and the fine particles were spherical. The volume average particle size measured by "Multisizer 3" (a particle size distribution analyzer by electric resistance method manufactured by Beckman Coulter) was 5 µm.

Hardness of the silicone elastomer constituting the silicone elastomer fine particles was measured as described below. Methylvinylpolysiloxane represented by the following formula (1), the methylhydrogenpolysiloxane represented by the following formula (2), and toluene solution of chloroplatinic acid-olefin complex (platinum content, 0.5%) were mixed at a ratio as described above, and the mixture was put in an aluminum dish to a thickness of 10 mm. After leaving at 25° C. for 24 hours, the mixture was heated in an incubator at 50° C. for 1 hour to produce a tack-free silicone elastomer. Hardness of the silicone elastomer measured by Durometer A was 29.

2,599 g of ion exchanged water at pH 5.8 was charged in a 3 liters glass flask equipped with an agitator having an anchor paddle, and after adjusting the temperature to 8 to 12° C., 104 g of methyltrimethoxysilane (an amount such that 43 parts by weight of polymethylsilsesquioxane was present after the hydrolytic condensation in relation to 100 parts by weight of the spherical fine silicone elastomer particles as described below) was added with agitation. The solution which was turbid after the addition became clear in about 10 minutes, confirming the progress of the hydrolysis. After agitating for further 1 hour, 231 g of aqueous dispersion of the spherical fine silicone elastomer particles as described above and 2.7 g of sodium N-myristoyl sarcosinate (anionic surfactant) (an amount such that 0.1 part by weight was present in relation to 100 parts by weight of the water at the addition of the alkaline substance as described below) were added, and the mixture was adjusted to a temperature of 8 to 12° C. Next, 3.0 g of 28% ammonia solution was added, and after agitation for 1 minute, the agitation was ceased. After 3 hours, the agitation was started, and 60 g of 28% ammonia solution was added. The mixture was heated to 55 to 60° C., and the mixture was heated for 1 hour while maintaining the temperature to complete the condensation. The pH of the water that had been added at the addition of the 60 g of the 28% ammonia solution was measured by adding 60 g of 28% ammonia solution to 2,599 g of water and water in the aqueous dispersion of the spherical fine silicone elastomer particles [total amount of water, 2,709 g], and measuring the pH of the mixture with a pH meter. The pH was 10.8.

The resulting aqueous dispersion of the silicone fine particles was dehydrated by a pressure filter to a moisture content of about 30%. The dehydrated product was moved to a 5 liters glass flask equipped with an agitator having an anchor paddle, and 3,000 g of water was added. After agitating for 30 minutes, the dispersion was dehydrated by a pressure filter. The dehydrated product was again moved to a 5 liters glass flask equipped with an agitator having an anchor paddle, and after adding 3,000 g of water, the dispersion was agitated for 30 minutes, and the dispersion was dehydrated by a pressure filter. The dehydrated product was moved to a 3 liters glass flask equipped with an agitator having an anchor paddle, and the product was heated in an oil bath at 120° C. with nitrogen bubbling to remove water, thereby obtaining silicone fine particles.

The resulting silicone fine particles were dispersed in water by using a surfactant, and measured for their diameter using a particle size distribution analyzer by electric resistance method "Multisizer 3" (manufactured by Beckman Coulter). The volume average particle size was 5 µm.

In the observation of the resulting silicone fine particles with the electron microscope, the fine particles were found to be in the form of the spherical fine silicone elastomer particles having polymethylsilsesquioxane semispheres with a size of 800 nm sparsely attached on its surface. The electron micrograph is shown in FIG. 1.

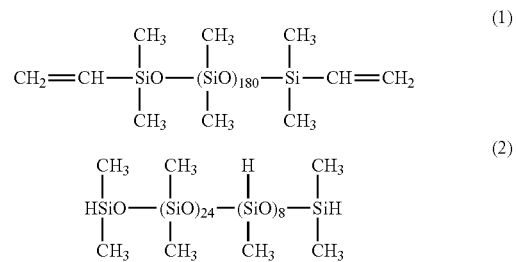

$$CH_2\!=\!CH-\underset{\underset{CH_3}{|}}{\overset{\overset{CH_3}{|}}{Si}}O-(\underset{\underset{CH_3}{|}}{\overset{\overset{CH_3}{|}}{Si}}O)_{180}-\underset{\underset{CH_3}{|}}{\overset{\overset{CH_3}{|}}{Si}}-CH\!=\!CH_2 \quad (1)$$

$$H\underset{\underset{CH_3}{|}}{\overset{\overset{CH_3}{|}}{Si}}O-(\underset{\underset{CH_3}{|}}{\overset{\overset{CH_3}{|}}{Si}}O)_{24}-(\underset{\underset{CH_3}{|}}{\overset{\overset{H}{|}}{Si}}O)_{8}-\underset{\underset{CH_3}{|}}{\overset{\overset{CH_3}{|}}{Si}}H \quad (2)$$

Example 2

The procedure of Example 1 was repeated except that the 2.7 g of sodium N-myristoyl sarcosinate (anionic surfactant) was replaced with 0.6 g of sodium N-myristoyl sarcosinate (anionic surfactant) and 2.1 g of lauryl sodium phosphate (anionic surfactant) (an amount such that 0.1 part by weight in total of the sodium N-myristoyl sarcosinate and the lauryl sodium phosphate is present in relation to 100 parts by weight of the water at the alkali addition as described below) to prepare silicone fine particles.

The resulting silicone fine particles were dispersed in water by using a surfactant, and the volume average particle size measured by "Multisizer 3" (a particle size distribution analyzer by electric resistance method manufactured by Beckman Coulter) was 6 µm.

Figure 2:
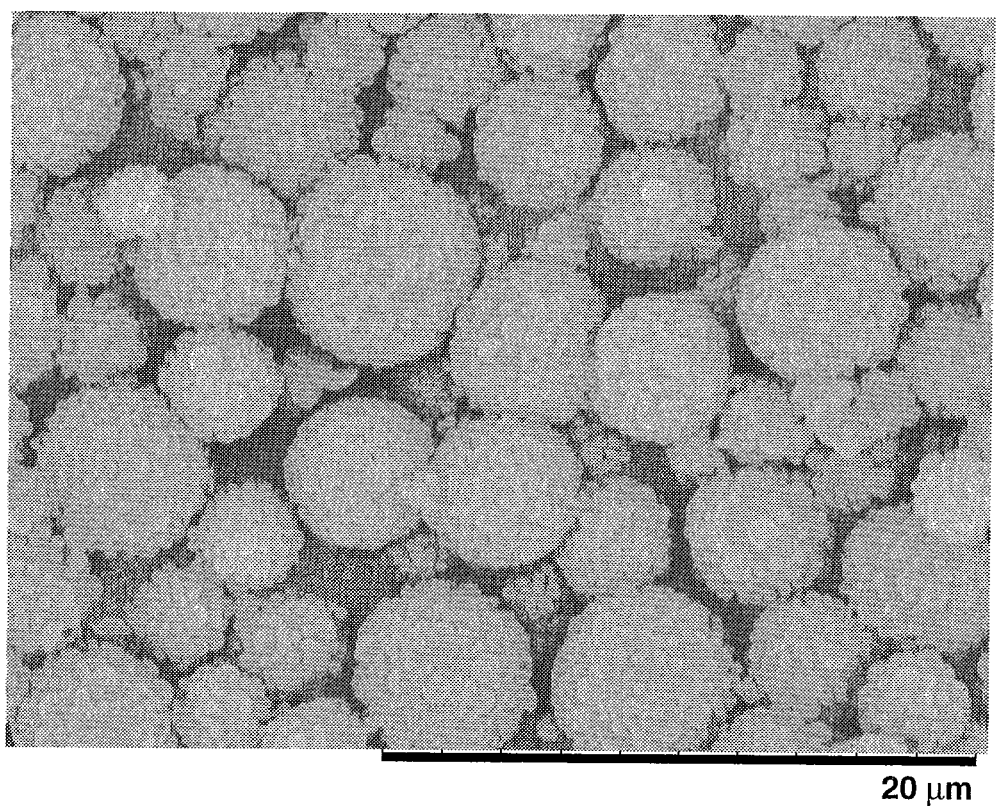
FIG. 2 is a photomicrograph of the silicone fine particles of Example 2.

In the observation of the resulting silicone fine particles with the electron microscope, the fine particles were found to be in the form of spherical fine silicone elastomer particles having polymethylsilsesquioxane spheres with the size of 400 nm to 500 nm attached on its surface at a high density. The electron micrograph is shown in FIG. 2.

Example 3

The procedure of Example 1 was repeated except that the 2.7 g of sodium N-myristoyl sarcosinate (anionic surfactant) was replaced with 9 g of 30% aqueous solution of sodium N-lauroylmethylalanine (anionic surfactant) (an amount such that 0.1 part by weight of the sodium N-lauroylmethylalanine was present in relation to 100 parts by weight of the water at the addition of the alkaline substance as described below) to prepare silicone fine particles.

The resulting silicone fine particles were dispersed in water by using a surfactant, and the volume average particle size measured by "Multisizer 3" (a particle size distribution analyzer by electric resistance method manufactured by Beckman Coulter) was 5 μm.

In the observation of the resulting silicone fine particles with an electron microscope, the fine particles were found to be in the form of spherical fine silicone elastomer particles having polymethylsilsesquioxane semispheres with a size of 700 nm sparsely attached on its surface.

Example 4

The procedure of Example 1 was repeated except that the 2.7 g of sodium N-myristoyl sarcosinate (anionic surfactant) was replaced with 2.7 g of sodium N-lauroylmethyltaurine (anionic surfactant) (an amount such that 0.1 part by weight was present in relation to 100 parts by weight of the water at the addition of the alkaline substance as described below) to prepare silicone fine particles.

The resulting silicone fine particles were dispersed in water by using a surfactant, and the volume average particle size measured by "Multisizer 3" (a particle size distribution analyzer by electric resistance method manufactured by Beckman Coulter) was 5 μm.

In the observation of the resulting silicone fine particles with an electron microscope, the fine particles were found to be in the form of the spherical fine silicone elastomer particles having polymethylsilsesquioxane semispheres with a size of 700 nm sparsely attached on its surface.

Example 5

2,164 g of ion exchanged water at a pH of 5.8 was charged in a 3 liters glass flask equipped with an agitator having an anchor paddle, and after adjusting the temperature to 8 to 12° C., 81 g of methyltrimethoxysilane (an amount such that polymethylsilsesquioxane after hydrolytic condensation was 11 parts by weight in relation to 100 parts by weight of the spherical fine silicone elastomer particle as described below) was added with agitation. After the addition, the solution which was turbid became clear in about 10 minutes, confirming the progress of the hydrolysis. After agitating for further 1 hour, 693 g of aqueous dispersion of the spherical fine silicone elastomer particles produced by repeating the procedure of Example 1 and 5.1 g of sodium polyoxyethylene lauryl ether sodium phosphate (anionic surfactant) (an amount such that 0.2 part by weight was present in relation to 100 parts by weight of the water at the addition of the alkaline substance as described below) were added, and the mixture was adjusted to a temperature of 8 to 12° C. Next, 3.0 g of 28% ammonia solution was added, and after agitating for 1 minute, the agitation was ceased. After 3 hours, the agitation was started, and 54 g of 28% ammonia solution was added. The mixture was heated to 55 to 60° C., and the mixture was heated for 1 hour while maintaining the temperature to complete the condensation. The pH of the water that had been added at the addition of the 54 g of the 28% ammonia solution was measured by adding 54 g of 28% ammonia solution to 2,164 g of water and water in the aqueous dispersion of the spherical fine silicone elastomer particles [total amount of water, 2,493 g], and measuring the pH of the mixture with a pH meter. The pH was 10.8.

The resulting aqueous dispersion of the silicone fine particles was dehydrated by a pressure filter to a moisture content of about 30%. The dehydrated product was moved to a 5 liters glass flask equipped with an agitator having an anchor paddle, and 3,000 g of water was added. After agitating for 30 minutes, the dispersion was dehydrated by a pressure filter. The dehydrated product was again moved to a 5 liters glass flask equipped with an agitator having an anchor paddle, and after adding 3,000 g of water, the dispersion was agitated for 30 minutes, and the dispersion was dehydrated by a pressure filter. The dehydrated product was moved to a 3 liters glass flask equipped with an agitator having an anchor paddle, and the product was heated in an oil bath at 120° C. with nitrogen bubbling to remove water, thereby obtaining silicone fine particles.

The resulting silicone fine particles were dispersed in water by using a surfactant, and the volume average particle size measured by "Multisizer 3" (a particle size distribution analyzer by electric resistance method manufactured by Beckman Coulter) was 5 μm.

In the observation of the resulting silicone fine particles with an electron microscope, the fine particles were found to be in the form of the spherical fine silicone elastomer particles having polymethylsilsesquioxane semispheres with a size of 400 and 800 nm sparsely attached on its surface.

Comparative Example 1

The procedure of Example 1 was repeated except that the 2.7 g of sodium N-myristoyl sarcosinate (anionic surfactant) was not used.

An attempt was made to disperse the resulting silicone fine particles in water by using a surfactant to thereby measure average particle size. The fine particles could not be dispersed due to the high agglomeration.

In the observation of the resulting silicone fine particles with the electron microscope, the fine particles were found to be a mixture of fine particles having a small amount of polymethylsilsesquioxane spheres having a size of 300 nm on the surface and polymethylsilsesquioxane spheres having a size of 300 nm not attached on the surface of the spherical fine silicone elastomer particles.

Comparative Example 2

864 g of an aqueous dispersion of spherical fine silicone elastomer particles prepared by repeating the procedure of Example 1 was charged in a 3 liters glass flask equipped with an agitator having an anchor paddle, and 1,993 g of water and 63 g of 28% ammonia solution were added. After adjusting the temperature to 8 to 12° C., 80 g of methyltrimethoxysilane (an amount such that 8.8 parts by weight of polymethylsilsesquioxane after the hydrolytic condensation was present in relation to 100 parts by weight of the spherical fine silicone elastomer particles) was added dropwise in 20 minutes while maintaining the solution temperature at 8 to 12° C. After agitating for further 1 hour, the dispersion was heated to 55 to 60° C., and the dispersion was agitated for 1 hour while maintaining the temperature to thereby complete the hydrolytic condensation of the methyltrimethoxysilane.

The resulting aqueous dispersion of the silicone fine particles was dehydrated by a pressure filter to a moisture content of about 30%. The dehydrated product was moved to a 5 liters glass flask equipped with an agitator having an anchor paddle, and 3,000 g of water was added. After agitating for 30 minutes, the dispersion was dehydrated by a pressure filter. The dehydrated product was again moved to a 5 liters glass flask equipped with an agitator having an anchor paddle, and after adding 3,000 g of water, the dispersion was agitated for 30 minutes, and the dispersion was dehydrated by a pressure filter. The dehydrated product was moved to a 3 liters glass flask equipped with an agitator having an anchor paddle, and the product was heated in an oil bath at 120° C. with nitrogen bubbling to remove water, thereby obtaining silicone fine particles.

The resulting silicone fine particles were dispersed in water by using a surfactant, and measured for their diameter using a particle size distribution analyzer by electric resistance method "Multisizer 3" (manufactured by Beckman Coulter). The volume average particle size was 5 µm.

In the observation of the resulting silicone fine particles with the electron microscope, the fine particles were found to be in the form of spherical fine silicone elastomer particles having polymethylsilsesquioxane spheres with a size of 80 to 100 nm attached on its surface at a high density.

Comparative Example 3

864 g of an aqueous dispersion of spherical fine silicone elastomer particles prepared by repeating the procedure of Example 1 was charged in a 3 liters glass flask equipped with an agitator having an anchor paddle, and 1,991 g of water, 63 g of 28% ammonia solution, and 2.4 g of sodium N-myristoyl sarcosinate (anionic surfactant) (an amount such that 0.1 part by weight was present in relation to 100 parts by weight of the water) were added. After adjusting the temperature to 8 to 12° C., 80 g of methyltrimethoxysilane (an amount such that 8.8 parts by weight of polymethylsilsesquioxane after the hydrolytic condensation was present in relation to 100 parts by weight of the spherical fine silicone elastomer particles) was added dropwise in 20 minutes while maintaining the solution temperature at 8 to 12° C. After agitating for further 1 hour, the dispersion was heated to 55 to 60° C., and the dispersion was agitated for 1 hour while maintaining the temperature to thereby complete the hydrolytic condensation of the methyltrimethoxysilane.

The resulting aqueous dispersion of the silicone fine particles was dehydrated by a pressure filter to a moisture content of about 30%. The dehydrated product was moved to a 5 liters glass flask equipped with an agitator having an anchor paddle, and 3,000 g of water was added. After agitating for 30 minutes, the dispersion was dehydrated by a pressure filter. The dehydrated product was again moved to a 5 liters glass flask equipped with an agitator having an anchor paddle, and after adding 3,000 g of water, the dispersion was agitated for 30 minutes, and the dispersion was dehydrated by a pressure filter. The dehydrated product was moved to a 3 liters glass flask equipped with an agitator having an anchor paddle, and the dispersion was heated in an oil bath at 120° C. with nitrogen bubbling to remove water, thereby obtaining silicone fine particles.

An attempt was made to disperse the resulting silicone fine particles in water by using a surfactant to thereby measure average particle size. The fine particles could not be dispersed due to the high agglomeration.

In the observation of the resulting silicone fine particles with the electron microscope, attachment of the polymethylsilsesquioxane particles on the surface of the spherical fine silicone elastomer particles was not observed.

In the case of the polymethylsilsesquioxane having the silicone fine particles attached on the surface of the Comparative Examples 1 to 3, the particles attached to the surface were either non-spherical particles or small-size particles with the size of 80 to 100 nm, and in the case of larger size particles of 300 nm, not all particles were attached to the surface and the amount of the particles attached were limited. On the other hand, in the case of the silicone fine particles of the Examples 1 to 5, the polymethylsilsesquioxane particles attached to the surface had a particle size of 400 to 900 nm, and the amount of the particles attached on the surface was also higher. Accordingly, these fine particles are expected to provide high light scattering property when incorporated in cosmetic products.

It is to be noted that the present invention is not limited to the embodiments as described above which are presented for the purposes of illustration, and any embodiments having the constitution substantially the same as the technical idea described in the claims with equivalent function and merits are within the scope of the present invention.

Japanese Patent Application No. 2011-226664 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for producing silicone fine particles, each particle comprising a spherical fine silicone elastomer particle and polyorganosilsesquioxane particles attached to the surface of the spherical fine silicone elastomer particle, comprising the steps of:
    adding an organotrialkoxysilane to water for hydrolysis to obtain organotrialkoxysilane hydrolysate; and
    adding spherical fine silicone elastomer particles having a volume average particle size of 0.5 to 100 µm, an anionic surfactant, and an alkaline substance to the organotrialkoxysilane hydrolysate and allowing the mixture to stand to thereby promote condensation of the organotrialkoxysilane hydrolysate, so that the polyorganosilsesquioxane is deposited on the surface of the spherical fine silicone elastomer particles, the polyorganosilsesquioxane particles have a particle size in the range of 200 to 2,000 nm, and the particle size of the polyorganosilsesquioxane particles is smaller than that of the spherical fine silicone elastomer particle.

2. A method for producing silicone fine particles according to claim 1 wherein the molar amount of the water in the hydrolysis of the organotrialkoxysilane is the same or more than the molar amount of the alkoxy group in the organotrialkoxysilane.

3. A method for producing silicone fine particles according to claim 1 wherein the anionic surfactant is added at an amount of 0.001 to 1 part by weight in relation to 100 parts by weight of the water.

4. A method for producing silicone fine particles according to claim 1 wherein the anionic surfactant used is at least one member selected from the group consisting of N-acyltaurate salt, N-acylamino acid salt, N-acylmethylalanine, alkyl phosphate, and polyoxyethylene alkyl ether phosphate.

5. A method for producing silicone fine particles according to claim 1 wherein the spherical fine silicone elastomer particles are added at an amount of 1 to 40 parts by weight in relation to 100 parts by weight of the water at the timing of the addition of the alkaline substance.

6. A method for producing silicone fine particles according to claim 1 wherein water after the addition of the alkaline substance is at a pH of 9 to 12.

7. A method for producing silicone fine particles according to claim 1 wherein the mixture is allowed to stand after the addition of the alkaline substance at a temperature of 0 to 60° C. for a period of 10 minutes to 24 hours.

8. Silicone fine particles comprising 100 parts by weight of spherical fine silicone elastomer particles having a volume average particle size of 0.5 to 100 μm and 1 to 100 parts by weight of a polyorganosilsesquioxane deposited on the surface of the silicone particles, the polyorganosilsesquioxane being in the form of particles having a particle size of 200 to 2,000 nm which is smaller than the spherical fine silicone elastomer particles.

9. The method for producing silicone fine particles according to claim 1, further comprising, after the step of allowing the mixture to stand to promote condensation, the step of heating the mixture to a temperature of 40 to 100° C. and/or the step of agitating the mixture, so as to complete the condensation of the organotrialkoxysilane hydrolysate.

10. A method for producing silicone fine particles, each particle comprising a spherical fine silicone elastomer particle and polyorganosilsesquioxane particles attached to the surface of the spherical fine silicone elastomer particle, comprising the steps of
    mixing an organotrialkoxysilane and water for hydrolysis to obtain organotrialkoxysilane hydrolysate;
    adding spherical fine silicone elastomer particles having a volume average particle size of 0.5 to 100 μm, an anionic surfactant, and an alkaline substance to the organotrialkoxysilane hydrolysate, while agitating a mixture; and
    stopping agitating and allowing the mixture to stand to promote condensation of the organotrialkoxysilane hydrolysate, so that the polyorganosilsesquioxane is deposited on the surface of the spherical fine silicone elastomer particles, the polyorganosilsesquioxane particles have a particle size in the range of 200 to 2,000 nm, and the particle size of the polyorganosilsesquioxane particles is smaller than that of the spherical fine silicone elastomer particle.

11. The method for producing silicone fine particles according to claim 10, wherein the mixture is allowed to stand after the addition of the alkaline substance at a temperature of 0 to 60° C. for a period of 10 minutes to 24 hours.

12. The method for producing silicone fine particles according to claim 10, further comprising, after the step of stopping and allowing the mixture to stand to promote condensation, the step of heating the mixture to 40 to 100° C. of a temperature and/or the step of agitating the mixture, so as to complete the condensation of the organotrialkoxysilane hydrolysate.

* * * * *